United States Patent
Dafforn et al.

(10) Patent No.: US 8,586,388 B2
(45) Date of Patent: Nov. 19, 2013

(54) MOLECULAR DETECTION SYSTEM

(75) Inventors: Timothy Richard Dafforn, Warwickshire (GB); Matthew Hicks, West Midlands (GB)

(73) Assignee: The University of Birmingham (GB)

( * ) Notice: Subject to any disclaimer, the term of this patent is extended or adjusted under 35 U.S.C. 154(b) by 995 days.

(21) Appl. No.: 12/514,043

(22) PCT Filed: Nov. 19, 2007

(86) PCT No.: PCT/GB2007/004405
§ 371 (c)(1),
(2), (4) Date: Nov. 16, 2009

(87) PCT Pub. No.: WO2008/059280
PCT Pub. Date: May 22, 2008

(65) Prior Publication Data
US 2010/0053619 A1    Mar. 4, 2010

(30) Foreign Application Priority Data
Nov. 17, 2006   (GB) .................................. 0622956.1

(51) Int. Cl.
*G01N 33/543* (2006.01)

(52) U.S. Cl.
USPC ........................................................ 436/524

(58) Field of Classification Search
None
See application file for complete search history.

(56) References Cited

U.S. PATENT DOCUMENTS

| | | | | |
|---|---|---|---|---|
| 5,083,026 A | * | 1/1992 | Elbaum | 250/369 |
| 5,268,305 A | * | 12/1993 | Ribi et al. | 436/501 |
| 5,672,691 A | * | 9/1997 | Kopetzki et al. | 530/413 |
| 2003/0104622 A1 | * | 6/2003 | Robbins et al. | 435/455 |

FOREIGN PATENT DOCUMENTS

| | | | | |
|---|---|---|---|---|
| EP | 410610 A2 | * | 1/1991 | G01N 21/19 |
| WO | WO00/04390 | | 1/2000 | |
| WO | WO02/079755 A2 | | 10/2002 | |

OTHER PUBLICATIONS

Chen (2003) PNAS 100: 4984-4989.*
Dafforn (2004) Biophy J 86: 404-410.*
Japanese Office Action dated Feb. 7, 2012.

* cited by examiner

*Primary Examiner* — Nc Yang
*Assistant Examiner* — Richard Moerschell
(74) *Attorney, Agent, or Firm* — Berliner & Associates

(57) ABSTRACT

A molecular sensor (10) comprises a flow path (12) configured for flowing a solution (28) potentially containing a target molecule (26). A source of polarized light (16) is provided and a detector (18) arranged to receive light from the source after it has passed through the flow path. A sensor element (19) is provided comprising a scaffold moiety (20) with a high aspect ratio disposed, in use, within the flow path and a receptor moiety (24), for the target molecule, attached to the scaffold moiety. A method for sensing a target molecule in a flowing solution is also described.

14 Claims, 1 Drawing Sheet

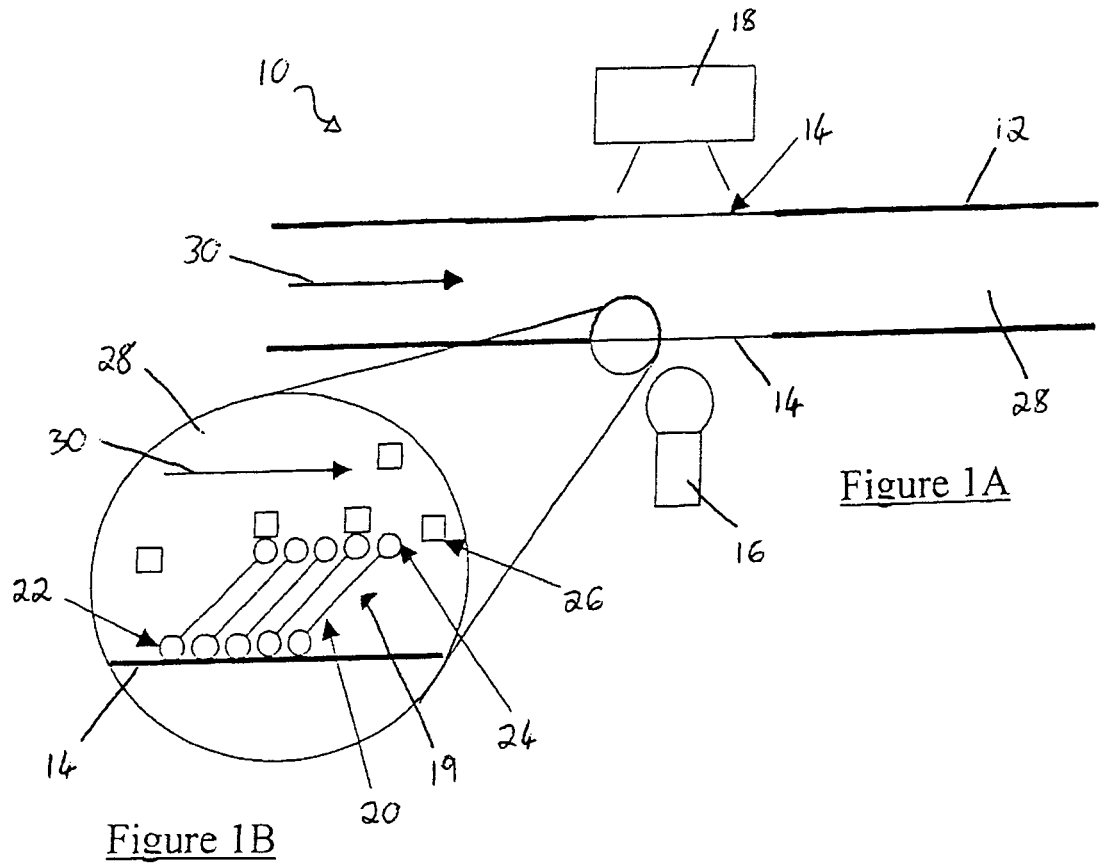
Figure 1A
Figure 1B
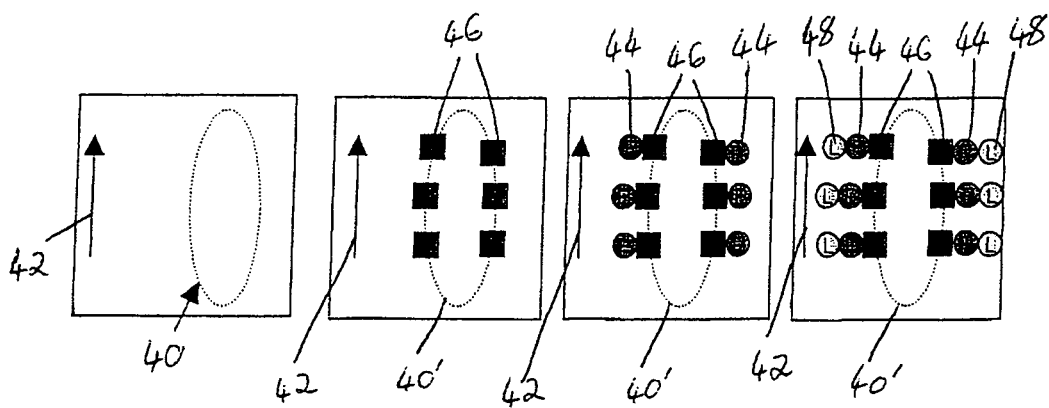
Figure 2A  Figure 2B  Figure 2C  Figure 2D

MOLECULAR DETECTION SYSTEM

FIELD OF THE INVENTION

This invention relates to a molecular detection system. Particularly, but not exclusively, the invention relates to a molecular sensor that utilises an optical phenomenon known as dichroism to identify the presence of specific molecules in a substance.

BACKGROUND TO THE INVENTION

By their nature, organisms contain many complex molecules and molecular assemblies. Some of the most important molecules and assemblies are large and have high aspect ratios (i.e. one axis significantly greater in length than any other). It is known to use an optical apparatus to specifically detect these high aspect ratio molecules. Such an apparatus relies on the way these long molecules interact with polarised light (i.e. light with an electric field established in one direction only).

The phenomenon being exploited in the above apparatus is known as dichroism. The incident light may be either linearly polarised, giving rise to linear dichroism (LD), or circularly polarised, giving rise to circular dichroism (CD). LD is the property exhibited by some molecular structures whereby linearly polarised light is differentially absorbed along two orthogonal axes. CD relates to the difference in absorption of left and right circularly polarised light. A molecule that is capable of selective light absorption is known as a chromophore. Dichroic molecules, i.e. those that exhibit dichroic properties, are a particular type of chromophore. Examples of dichroic materials are certain natural crystals, stretched polymers, and other non-isotropic molecules. Biomolecules contain a wide range of chromophores (including aromatic side chains, nucleotides and peptide backbones).

In order to be able to observe a dichroic effect, it is necessary that the chromophores be aligned, or at least partially aligned, with respect to the incident polarised light beams. This requirement has the advantage of allowing the extraction of data only from aligned molecules in a milieu of unaligned molecules. However, this requirement has, to date, also limited the application of the above technique, primarily, to the study of large molecules with high aspect ratios, since these are easily alignable. A molecule is considered to have a high aspect ratio if one axis is substantially longer than the other. Suitable molecules may be in the shape of a rod, a disc or a cruciform. Depending upon the stiffness of the molecule, an aspect ratio of 100:1 may be sufficient to facilitate alignment but an aspect ratio of greater than 1000:1 is preferable. Some examples of moieties of interest that have been successfully aligned include linear biomolecules in the form of DNA, fibrous proteins and membranes (including membrane proteins) (Marrington R, Small E, Rodger A, Dafforn T R, Addinall S G, "FtsZ fiber bundling is triggered by a conformational change in bound GTP" J Biol Chem 2004; 279(47):48821-48829; Dafforn T R, Rajendra J, Halsall D J, Serpell L C, Rodger A, "Protein fiber linear dichroism for structure determination and kinetics in a low-volume, low-wavelength couvette flow cell" Biophys J 2004; 86(1 Pt 1):404-410; Dafforn T R, Rodger A, "Linear dichroism of biomolecules: which way is up?" Curr Opin Struct Biol 2004; 14(5):541-546; Halsall D J, Rodger A, Dafforn T R, "Linear dichroism for the detection of single base pair mutations" Chem Commun (Camb) 2001 (23):2410-2411).

A particularly convenient method for aligning such molecules is to create a solution including the molecules and then to flow the solution. Due to the elongate nature of the molecules, alignment arises as a result of shear forces generated by the flow, making the sample suitable for exhibiting the effect of linear dichroism.

In a known apparatus, once the molecules of interest have been aligned, linearly polarised light is directed through the solution from a direction substantially perpendicular to the axes of the aligned molecules. Absorption of light occurs within a molecule because, at a particular wavelength, the electric field of radiation urges the electrons in the molecule in a particular direction. When several molecules are similarly aligned, the electrons in each are all characterised by the same preferred net displacement direction. LD is a measure of the difference of absorbance of the incident light between two orthogonal polarisations. Varying the wavelength of the incident light and detecting the light emerging from the sample, allows a spectrum to be obtained which illustrates the absorbance of the sample with respect to wavelength.

An LD spectrum of a molecule provides information on the chromophores that are present including the orientation of the chromophores (and hence molecular conformation) and the orientation of the chromophores with respect to the axes of polarization. This information is important in understanding the structure of the molecule. Note that LD is a measurement of a sample's bulk property. The strength of the absorbance can be used to quantify the number of target molecules that are present in the sample. In addition, since LD is extremely sensitive to changes in alignment, an anomaly in the structure of a molecule may be detected. For example, LD can detect the distortion caused by a single mismatched hydrogen bond in a 1300 bp (base pair) fragment of DNA.

Furthermore, LD is extremely sensitive to the formation of a complex since the binding of an aligned molecule to a second molecule has the following two measurable effects.

1) The shape of the aligning moiety is altered and this results in its alignment also being altered, which leads to a change in the observed LD spectrum.
2) The second molecule itself becomes aligned by virtue of its attachment to the aligned molecule. This leads to the generation of an LD signal for the previously unaligned chromophores of the second molecule. Thus, information on the structure of the complex can be obtained.

Both of the above effects result in detectable phenomena that can be used to detect the formation of complexes. Not only can structural information be gleamed regarding the nature of the complex but the affinity of the interaction can also be determined.

Unfortunately, most molecules do not have a high aspect ratio and instead have shapes more closely related to spheres, with aspect ratios of less than approximately 5:1. In order to align these molecules it is necessary to link the target molecule to a receptor that itself has a high aspect ratio. This method of alignment has been achieved and has been applied to studies of ligands (e.g. cisplatin) that bind to naturally alignable receptors (e.g. DNA). However, this method is also limited in its application since only those molecules that bind to naturally alignable receptors can be studied.

It is therefore an aim of the present invention to expand the application of dichroic analysis.

SUMMARY OF THE INVENTION

According to a first aspect of the present invention there is provided a molecular sensor comprising a flow path configured for flowing a solution potentially containing a target molecule; a source of polarised light; a detector arranged to receive light from the source after it has passed through the flow path; and a sensor element comprising a scaffold moiety with a high aspect ratio disposed, in use, within the flow path and a receptor moiety, for the target molecule, attached to the scaffold moiety.

In this specification the term 'high aspect ratio' relates to an aspect ratio of at least 75:1 and preferably at least 100:1.

According to a second aspect of the present invention there is provided a sensor element for use in the sensor of the first aspect of the invention, said sensor element comprising a scaffold moiety with a high aspect ratio and attached thereto a receptor moiety, said receptor moiety having a selective binding affinity for a target molecule of interest.

Thus, the first aspect of the invention provides a molecular sensor that can be used to detect whether a target molecule is present in a solution. Advantageously, the use of an alignable scaffold moiety as a substrate for the attachment of a receptor moiety means that neither the receptor moiety itself nor the target molecule requires inherent alignment properties. Similarly, the scaffold moiety itself need not be chromophoric. Due to the alignment capabilities of the sensor, the dichroic properties of the target molecules can be assessed. Thus, as well as being able to identify the aligned molecules through the resulting dichroic spectrum, the sensor can be used to quantify the aligned molecules and to detect the presence of molecular anomalies such as mismatches. The binding properties of the receptor moiety and target molecule may also be studied using the sensor. The inherent nature of dichroic molecules means that the sensor is extremely sensitive.

Preferably, the target molecule is dichroic. Alternatively, or additionally, the receptor moiety may be dichroic. Where the target molecule is not dichroic, it is essential that the dichroic signal of the receptor moiety changes upon binding with the target molecule. Preferably, the scaffold moiety is not dichroic.

Preferably, the sensor comprises a plurality of scaffold moieties.

Preferably, the or each scaffold moiety has a plurality of receptor moieties attached thereto. Preferably each receptor moiety is arranged to bind with the same target molecule. Alternatively, the receptor moieties may be arranged to bind with different target molecules.

Preferably, the or each scaffold moiety is anchored in the flow path such that, in use, the or each scaffold moiety is capable of alignment in a flow but its location is fixed within the flow path.

Although reference is made to a scaffold moiety as a single entity, it will be understood that the scaffold may be constructed from two or more components serving different functions (e.g. anchoring in the flow path, attachment to the receptor, or other physical or chemical functions).

Preferably, the flow path is provided in a flow cell such as a cuvette flow cell or a capillary flow cell, which is rotated to generate flow in the solution. Alternatively, the flow path is provided in a pipe and passing the solution through the pipe generates flow. In each case, it will be understood that shear flow is required for stable alignment of the target molecules.

Preferably, the solution is provided in aqueous phase so as to enable the sample to be easily flowed. Alternatively, the solution may be in the form of a gas or a powder, both of which can be flowed.

Preferably, the light source is configured to emit linearly polarised beams of light. More preferably, the light source is configured to emit two orthogonal beams of linearly polarised light.

Preferably, the light source is a linear dichroic spectroscope.

Preferably, the detector is configured to generate a spectrum that illustrates the absorbance of the solution with respect to wavelength.

Preferably, the light source and detector are arranged to emit and detect light respectively passing perpendicularly to the flow direction.

According to a third aspect of the invention there is provided a method for sensing a target molecule in a flowing solution comprising providing in a flow path a scaffold moiety with a high aspect ratio and having a receptor moiety, for the target molecule, attached thereto; flowing a solution potentially containing a target molecule along the flow path; passing polarised light through the flow path; and detecting the polarised light after it has passed through the flow path.

It will be understood that flowing the solution aligns the scaffold/receptor moiety with the direction of flow. It also allows the target molecule to bind with the receptor moiety. In so doing, the target molecules are also aligned within the flow, thereby making them detectable through their dichroic properties.

The third aspect of the present invention provides a method for sensing target molecules that were previously non-detectable because they were non-alignable. The use of an alignable scaffold moiety as a substrate for the attachment of a receptor moiety means that the receptor moiety itself does not require inherent alignment properties. Consequently, the above method can be used to detect target molecules which are not inherently alignable and which do not bind with an inherently alignable receptor moiety. As such, the third aspect of the present invention has a broad application and may be used, for example, to detect DNA, proteins and organic compounds, which have hitherto been undetectable.

In addition to the above, the third aspect of the invention provides a simple method for sensing target molecules. The method is relatively cheap to employ and is robust since there are relatively few components involved.

Possible applications of the above three aspects of the invention include the alignment and detection of chemical or biological molecules in a flowing liquid, e.g. in a pipe or capillary tube. Thus, allowing for the detection or assay of such molecules in flow injection devices or in water distribution pipes.

BRIEF DESCRIPTION OF THE DRAWINGS

FIG. 1A illustrates schematically a molecular sensor according to the present invention;

FIG. 1B shows an enlarged view of a portion of the molecular sensor of FIG. 1A, illustrating the method of the present invention;

FIG. 2A illustrates schematically a scaffold according to the present invention;

FIG. 2B illustrates schematically the scaffold of FIG. 2A with attachment points for receptors;

FIG. 2C illustrates schematically the scaffold of FIG. 2B with receptors attached to the attachment points; and FIG. 2D illustrates schematically the scaffold of FIG. 2C with target molecules attached.

DETAILED DESCRIPTION OF CERTAIN EMBODIMENTS

With reference to FIG. 1A, there is illustrated a molecular sensor 10 according to the present invention. The sensor 10 comprises a flow path in the form of an elongate pipe 12 that is mostly made from plastic and is opaque. The central portion of the pipe 12 is configured as an observation window 14 and is made from a material that is transparent to the wavelength of light employed. In this particular example, the observation window 14 is made from glass quartz, which is transparent to visible light. Thus, in this example the observation window 14 is configured to allow light in the wavelength range of approximately 400 nm to 700 nm to pass therethrough. Adjacent one side of the observation window 14 is a light source 16. The light source 16 is configured to emit two orthogonal linearly polarised beams of light through the observation window 14 and thereby through the flow path. Disposed opposite to the light source 16, on the other side of the observation window 14 and the flow path, is a detector 18. The detector 18 is configured to detect the light beams emitted by the light source 16 once they have passed through the observation window 14 and the flow path.

As illustrated in FIG. 1B, a plurality of sensor elements 19 are provided in the region of the observation window 14. Each sensor element 19 comprises a scaffold moiety 20 and a receptor moiety 24. Each scaffold moiety 20 has an elongate molecular structure with an aspect ratio of approximately 1000:1 and can be considered to be a rigid linker. One end of each scaffold moiety 20 is attached to the inside of the observation window 14 via an anchor region 22 that holds the ends of each respective scaffold moiety 20 in a fixed location within the observation window 14. The free end of each scaffold moiety 20 is linked with a receptor moiety 24. The receptor moiety 24 is attached to the scaffold moiety 20 in such a way that it is free to bind with its associated target molecule 26. Thus, the receptor moieties 24 can be considered as "bait" for the target molecules 26.

In use, a liquid solution 28, which includes target molecules 26, is flowed through the pipe 12 in the direction indicated by arrow 30 in FIGS. 1A and 1B. This flow 30 causes the scaffold moieties 20 to align in a regular fashion along the length of the observation window 14. When the target molecules 26 flow sufficiently close to the receptor moieties 24 they will become bound to the receptor moieties 24. As the scaffold moieties 20 are all regularly aligned so too are all the receptor moieties 24. Thus, when the target molecules 26 bind with the receptor moieties 24, they too are aligned.

Once the receptor/target molecule complexes are aligned they will begin to absorb some of the linearly polarised light emitted by the light source 16. Consequently, less light will reach the detector 18 when the target molecules 26 are present. This enables the detector 18 to determine whether or not the target molecules 26 are present in the solution 28. The detector 18 is capable of producing a spectrum illustrating the absorbance of the solution 28 with respect to wavelength. This information can be used to monitor the nature, alignment, quantity and structure of the target molecules 26 since changes in each of these factors will result in a change in the observed spectra. Monitoring the flow 30 over time also enables information to be gleaned regarding the affinity of the interaction between the receptor moieties 24 and the target molecules 26. Consequently, the molecular sensor 10 of the present invention can serve as an in-line continuous flow measurement device.

There are various structures that can serve as suitable alignable scaffold moieties 20. In particular, it has been shown that although membrane proteins are not inherently alignable in fluid flow, membranes in the form of vesicles are alignable. Such a membrane vesicle 40 is illustrated schematically in FIG. 2A. In this instance, the flow indicated by arrow 42 induces deformation of the membrane vesicle 40 into an elongate ellipsoid that is aligned with the flow 42. Any membrane proteins (not shown) that are contained in the membrane vesicle 40 are also similarly aligned with the flow 42.

The above use of a membrane vesicle 40 has been expanded through the present invention to facilitate the alignment of any target molecule in the form of a ligand 48, as illustrated in FIG. 2D. In this case, extrusion is used to produce lipid vesicles 40', shown in FIGS. 2B, 2C and 2D. Preferably, the vesicles 40' are phospholipid vesicles approximately 100 nm in length. Such vesicles 40' are not dichroic and therefore they produce very little interfering signal. Similar vesicles 40' with an average length of between 100 nm and 140 nm are also suitable. In addition to the standard lipids used to make the known vesicles 40, these vesicles 40' include attachment points in the form of derivatised lipids 46 that are designed to form a tight complex with a complementary region of the receptor, which in this case is a protein 44. An example of a suitable derivatised lipid 46 is the nickel salt of 1,2-dioleoyl-sn-glycero-3-{[N(5-amino-1-carboxypentyl) iminodiacetic Acid]succinyl} (DOGS-NTA-Ni). This particular lipid derivative 46, which is part of the vesicle 40' structure, is able to form a tight complex with a histidine cluster (not shown) in protein 44. Hexa-histidine clusters form the basis of the most common method for immobilization of proteins (via a six histidine tag on the protein) and as such provide an ideal part of the protein 44 for attachment to the vesicle 40'. Thus, in this embodiment the vesicle 40' constitutes the scaffold moiety and the protein 44 constitutes the receptor moiety. It will be noted that each vesicle 40' comprises a plurality of receptor moieties. Target molecules in the form of ligands 48 for protein 44 are able to bind with a binding domain of the receptor moiety (protein 44) as shown in FIG. 2D. As a result of the alignment of the vesicle 40' in the flow 42, the ligands 48 are also aligned when attached to the proteins 44 and so they can be detected by the molecular sensor shown in FIG. 1A.

The scaffold moieties 20 in the above examples may be employed in free flow or may be directly attached, or anchored, to the observation window 14. In one embodiment, the scaffold moieties 20 (for example, the vesicles 40') may be applied to the internal surface of the observation window 14 as a thin film. Alternatively, the internal surface of the observation window 14 may be chemically derivatised to allow attachment of the scaffold moiety 20.

Alternative attachment systems for linking a receptor moiety to a lipid vesicle may employ any covalent or non-covalent linkage that can be added to the lipid and then incorporated into the vesicle. Such systems might include the use of thiol and amine reactive groups or biotin. It is an important feature of these designer-vesicles that they only form complexes with the protein (or other receptor) of choice (e.g. those containing the part of the molecule designated for attachment, such as the hexa-histidine tag). This is important because if there is no selectivity in the interaction between the alignable scaffold and the receptor then other constituents in the fluid that is being studied (which may be, for example, a complex mixture of blood or serum) could attach to the scaffold and produce an LD signal which would interfere with the real signal and therefore lead to false positives. In the embodiment described, the hexa-histidine tag was chosen to be used in selective purifications therefore eliminating any undesirable binding. Other systems could be employed, such as Biotin-avidin linkages, which could provide the necessary selectivity.

Controls to eliminate absorption data due to non-targeted associations may be applied to the molecular sensor 10 of the present invention. For example, a range of scaffold moieties 20 (i.e. vesicles 40') that include differently charged receptor moieties 24 (i.e. proteins 44) can be employed and a range of commonly available molecules not containing the part of the molecule targeted for attachment can be flowed in solution past the scaffold moieties 20 and any binding measured using LD. The resulting signal can then be taken as an indication of background noise and this information can be used to produce a greater signal-to-noise ratio when the apparatus is used to detect only the target molecules 26.

Another alternative system according to the present invention, involves the use of long chain organic polymers, which have the correct hydrodynamic properties for forming alignable scaffold moieties, while containing functional chemical groups, which can be derivatised with receptor moieties. Such organic polymers would have a high aspect ratio and could either be disc, cruciform or rod shaped. Specific examples of suitable scaffold moieties include Chitin and Polyethylene Glycol.

A yet further embodiment of the present invention employs phage. Filamentous phage, such as M13, are formed of a long tube of proteins (approximately 500 nm long and 5 nm in diameter) surrounding a piece of DNA. Accordingly, phage can act as scaffold moieties that can align in shear flow. Once aligned, the Applicants have found that the proteins within the phage produce a large LD signal that can be measured. They have also shown that the binding of a ligand to receptors on the surface the phage alters its LD signal. While this alteration in the LD signal may be the result of either an overall alteration in the hydrodynamic properties of the phage or the appearance of spectral features from the now aligned ligand, the Applicants have shown that this can be used to measure the ligand-to-phage affinity.

Advantageously, immunoglobulins or other proteins on the phage surface that can serve as receptors have affinities for specific target molecules. Thus, not only can specific phage strains be used to detect the presence of specific bacteria such as *E. coli, C. Dificile*, MSRA or VRSA, but also genetically modified phage can be produced to detect the presence of ligands such as SARS, tuberculosis, HIV and hepatitis. Accordingly, embodiments of the present invention can be employed in a large number of applications.

In the embodiment of FIGS. 1A and 1B, the elongate pipe 12 need not be plastic and may be made from other biocompatible materials. The observation window 14 may be made from sapphire, which allows transmission of visible light, or from quartz or CaF, which are transparent to ultraviolet wavelengths. Generally, the wavelength range of approximately 180 nm to 800 nm is appropriate for most applications. However, other suitable materials may be used to form an observation window 14 with the desired transmissive properties.

It will be appreciated by persons skilled in the art that various modifications may be made to the above-described embodiments without departing from the scope of the present invention. For example, whilst the above discussion has been primarily concerned with the alignment and detection of biomolecules, the invention is equally applicable to other molecules.

The invention claimed is:

1. A molecular sensor for detecting a target molecule in a solution using dichroism, the sensor comprising:
   a flow path configured for flowing a solution potentially containing the target molecule;
   a source of polarized light;
   a detector arranged to receive light from the source after it has passed through the flow path; and
   a sensor element for use in the flow path, the sensor element comprising a plurality of scaffold moieties, each with an aspect ratio of at least 75:1, wherein each scaffold moiety is alignable by the flow of the solution, the sensor element further comprising a receptor moiety, for the target molecule, attached to each scaffold moiety.

2. The molecular sensor according to claim 1 wherein the receptor moiety is dichroic.

3. The molecular sensor of claim 1 wherein each scaffold moiety is not dichroic.

4. The molecular sensor of claim 1 comprising a plurality of sensor elements, each sensor element comprising a scaffold moiety and a receptor moiety.

5. The molecular sensor of claim 1 wherein each scaffold moiety has a plurality of receptor moieties attached thereof.

6. The molecular sensor of claim 5 wherein each receptor moiety has the same binding affinity for a specific target molecule.

7. The molecular sensor of claim 1 wherein each scaffold moiety is anchored in the flow path such that each scaffold moiety is capable of alignment in a flow but its location is fixed within the flow path.

8. The molecular sensor of claim 1 additionally comprising a flow cell which is rotatable to generate flow in the solution.

9. The molecular sensor of claim 1 additionally comprising a pipe such that in use passing the solution through the pipe generates flow.

10. The molecular sensor of claim 1 wherein the light source is a source of linearly polarized beams of light.

11. The molecular sensor of claim 1 wherein the light source is a linear dichroic spectroscope.

12. The molecular sensor of claim 1 wherein the detector is one which generates a spectrum that illustrates the absorbance of the solution with respect to wavelength.

13. The molecular sensor of claim 1 wherein the light source and detector are arranged to respectively emit and detect light passing perpendicularly to the flow direction.

14. The sensor element for use in the sensor of claim 1 said sensor element comprising a plurality of scaffold moieties, each with an aspect ratio of at least 75:1, wherein each scaffold moiety is alignable by solution flow and is attached to at least one receptor moiety, said at least one receptor moiety having a selective binding affinity for a target molecule of interest.

* * * * *